US006780866B2

(12) United States Patent
Ku et al.

(10) Patent No.: US 6,780,866 B2
(45) Date of Patent: Aug. 24, 2004

(54) ANALGESIC COMPOSITION AND METHOD

(75) Inventors: Baoshan Ku, Beijing (CN); Frank Hay Kong Shum, North Point (HK)

(73) Assignee: WEX Medical Instrumentation Co., Ltd., Hong Kong (CN)

(*) Notice: Subject to any disclaimer, the term of this patent is extended or adjusted under 35 U.S.C. 154(b) by 0 days.

(21) Appl. No.: 10/062,483

(22) Filed: Feb. 5, 2002

(65) Prior Publication Data

US 2002/0198226 A1 Dec. 26, 2002

(30) Foreign Application Priority Data

May 18, 2001 (CN) ........................................ 01118098 A

(51) Int. Cl.$^7$ ...................... A61K 31/505; A61K 31/44; A61K 39/395

(52) U.S. Cl. ..................... 514/267; 514/282; 424/183.1

(58) Field of Search ................................ 514/267, 282, 514/183, 287, 292, 295; 424/183.1

(56) References Cited

U.S. PATENT DOCUMENTS

| | | | | | |
|---|---|---|---|---|---|
| 4,906,779 | A | * | 3/1990 | Weber et al. | 564/238 |
| 5,846,975 | A | * | 12/1998 | Pan et al. | 514/282 |
| 5,859,186 | A | * | 1/1999 | Justice et al. | 530/324 |
| 6,030,974 | A | * | 2/2000 | Schwartz et al. | 514/267 |
| 6,407,088 | B1 | * | 6/2002 | Dong et al. | 514/183 |
| 6,451,554 | B1 | * | 9/2002 | Wood et al. | 435/69.1 |
| 6,559,154 | B2 | * | 5/2003 | Kang et al. | 514/267 |
| 6,599,906 | B1 | * | 7/2003 | Ku et al. | 514/257 |
| 2002/0119987 | A1 | * | 8/2002 | Kang et al. | 514/267 |

FOREIGN PATENT DOCUMENTS

WO WO95/23132 * 8/1995

OTHER PUBLICATIONS

Pu et al., A novel analgesic toxin(hannalgesin) from the venom of king cobra (*ophiophangus hannah*), Database CAPLUS AN 1995:967046, (abstract only), Toxicon (1995), vol. 33(11), pp. 1425–1431.*

Sanchez–Blazquez et al., Cholera toxin and pertussis toxin . . . , Database CAPLUS, AN 1991:223213, (abstract), Life Sciences. 1991, Vo. 48(18), pp. 1721–1727.*

Sanchez–Blazquez et al., Both pertussis toxin and potassim chloride, given icv reduce the efficcy of opioids . . . , Database CAPLUS, AN 1989:587352, (abstract), Advances in the Biosciences (OXford), 1989, vol. 75, p. 451–454.*

Basilico et al., Influence of omega–conotoxin on morphine analgesia and withdrawal syndrom in rats., Database CAPLUS, AN 1992:584676, (abstract), European Journal of Pharmacology, 1992, vol. 218(1), p. 75–81.*

D. Besse et al., Brain Research, vol. 548, (1991), pp. 287–291.

Y.T. Wang et al., Acta Physiologica Sinica, vol. 47, No. 3, (1995), pp. 253–258.

C.–F. Hung et al., British Journal of Anesthesia, vol. 81, (1998), pp. 925–931.

William A. Catterall, Physiological Reviews, vol. 72, No. 4, (Oct. 1992), pp. s15–s18.

P.G. Kostyuk et al., Neuroscience, vol. 6, No. 12 (1981), pp. 2423–2430.

Srdija Jeftinija, Brain Research, vol. 639, (1994), pp. 125–134.

R.A. North et al., J. Physiol., vol. 364, (1985), pp. 265–280.

* cited by examiner

*Primary Examiner*—Vickie Kim
(74) *Attorney, Agent, or Firm*—Birch, Stewart, Kolasch & Birch LLP

(57) ABSTRACT

A pharmaceutical analgesic composition comprising an opioid analgesic agent and a compound that binds to the SS1 or SS2 subunit of a sodium channel, such as tetrodotoxin and saxitoxin, and analogs thereof. Administration of an opioid analgesic agent and a compound that binds to the SS1 or SS2 subunit of a sodium channel, such as tetrodotoxin and saxitoxin, and analogs thereof, produces analgesia in the treatment of pain in mammals.

14 Claims, 5 Drawing Sheets

Fig 1. Analgesia effect of co-administered TTX and morphine: formalin test in rats.
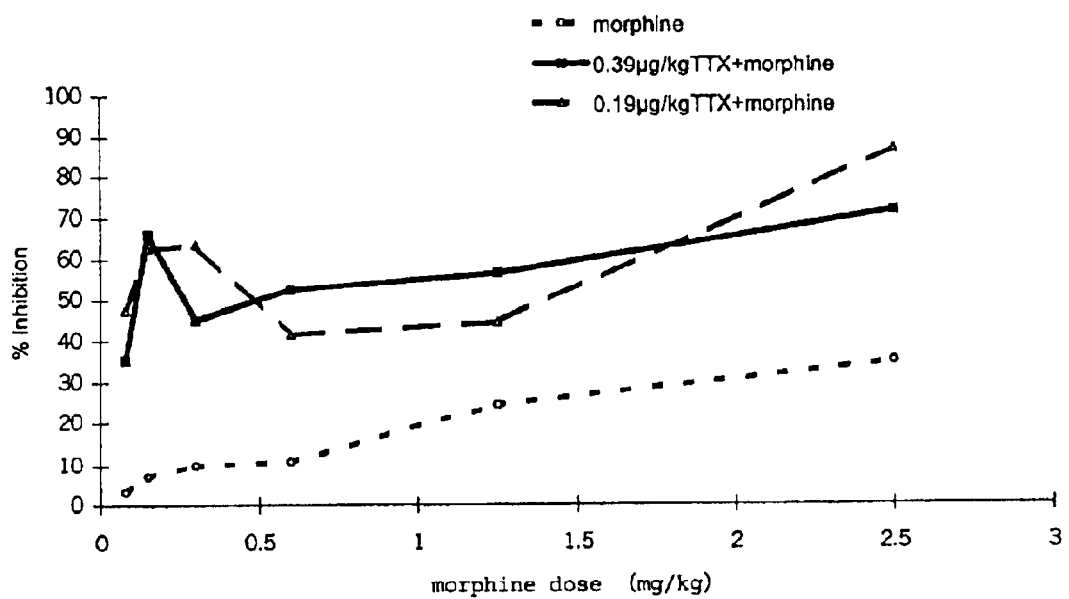

Fig 2. Analgesia effect of co-administered TTX 0.19 µg and morphine: formalin test in rats.
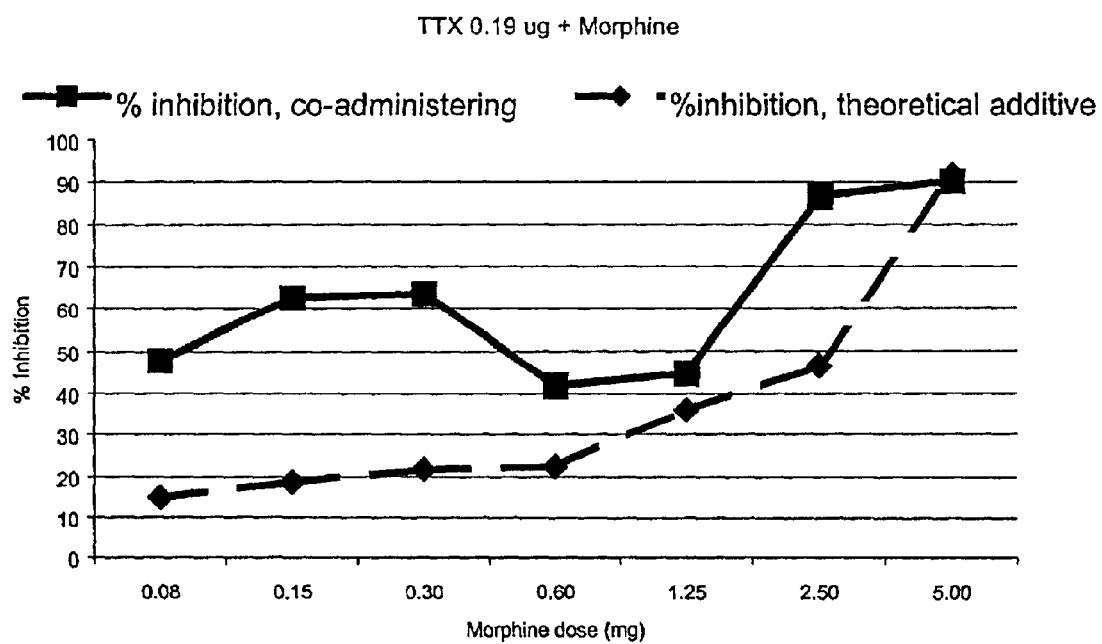

Fig 3. Analgesia effect of co-administered TTX 0.39 µg and morphine: formalin test in rats.
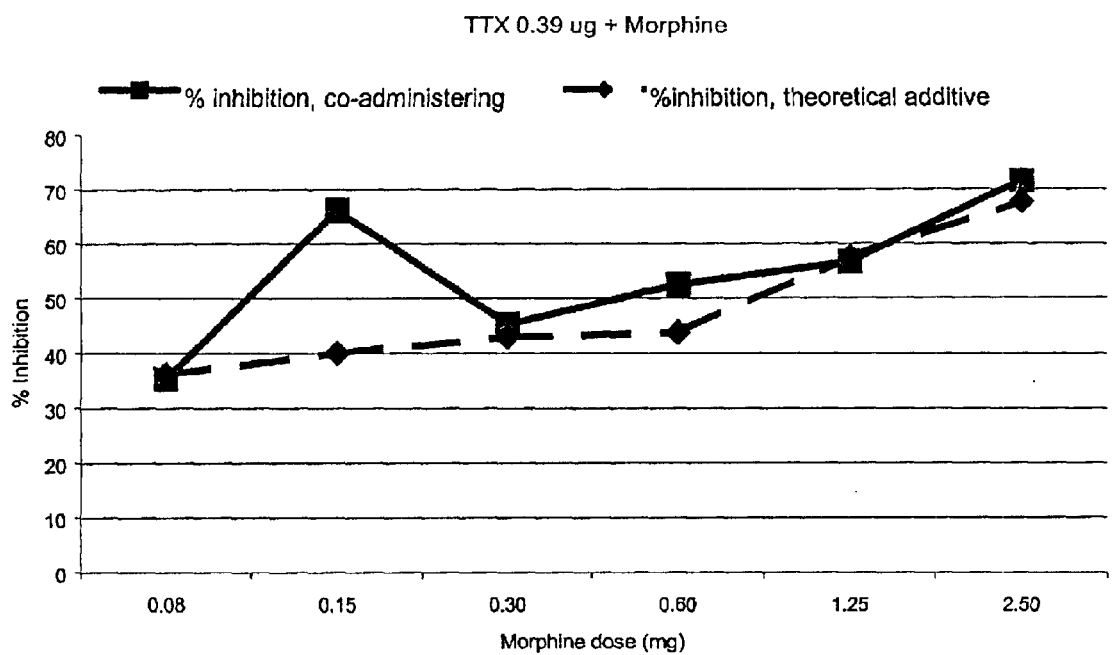

Fig 4. Analgesia effect of co-administered TTX 0.39 µg/kg and morphine: tail-flick test in mice.
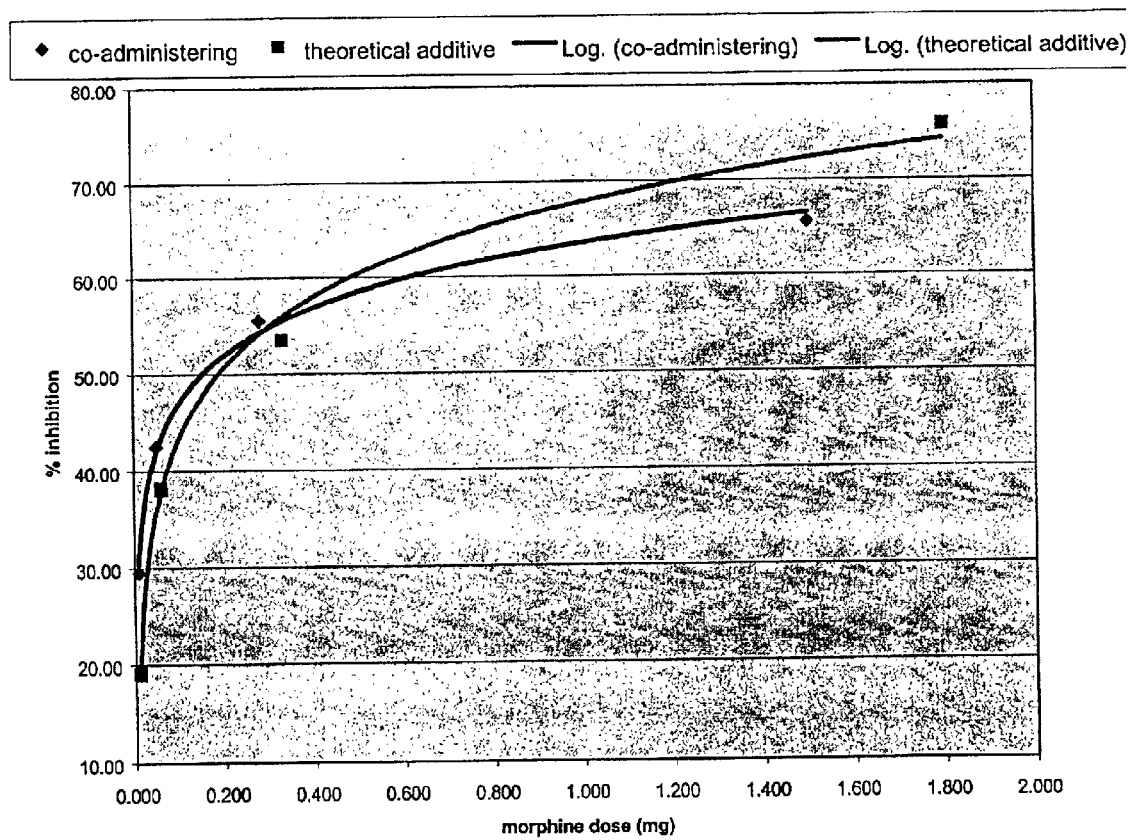

Fig 5. Analgesia effect of co-administered TTX 0.79 µg/kg and morphine: tail-flick test in mice.
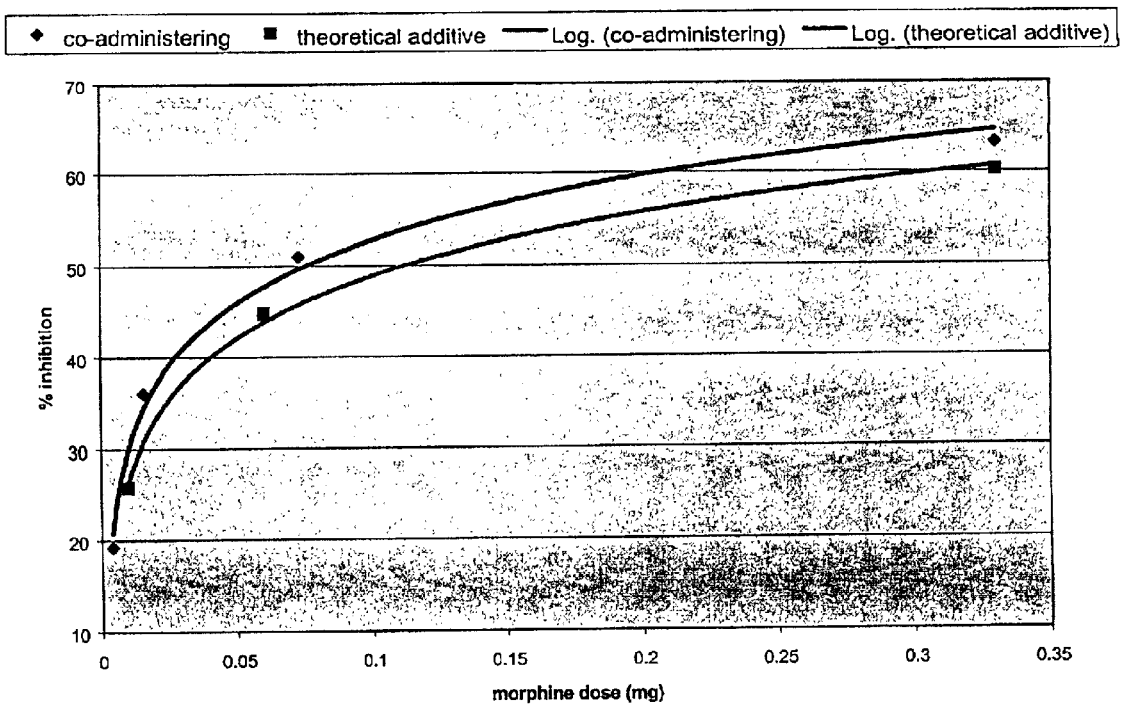

ANALGESIC COMPOSITION AND METHOD

This nonprovisional application claims priorty under 35 U.S.C. § 119(a) on Patent Application No. 01118098.6 filed in China on May 18, 2001, which is herein incorporated by reference.

FIELD OF INVENTION

The present invention relates to a method of producing analgesia in a mammal experiencing pain, comprising administering to the mammal a composition comprising a synergistically effective analgesic combination of an opioid analgesic agent and a compound that binds to the SS1 or SS2 subunit of a sodium channel in a pharmaceutically suitable vehicle.

BACKGROUND OF THE INVENTION

According to U.S. Pat. No. 6,150,524, opioid analgesics such as morphine are the most powerful analgesics for treating severe chronic and acute pain. An example of chronic pain is the pain experienced by cancer patients. An example of acute pain is the pain experienced after operations. The pain relieving activity of opioid analgesics includes a depressive effect on the central nervous system. The analgesic activity of opioid analgesics such as morphine and deltorphin II can be mediated via different opioid receptors, for example, via $\mu$-opioid and $\delta$-opioid receptors. Opioid analgesics are invaluable for the treatment of severe acute or chronic pain as, for example, may occur in bone degenerative diseases and cancer conditions. They are easy to administer and they provide effective pain relief in most patients. Due to the excellent overall tolerability of opioids, the doses of morphine and other strong opioids can be increased to relatively high levels.

The opioids used for treating such pain are indeed highly effective but have a number of unpleasant and/or undesirable side effects (e.g. a short duration of activity, respiratory depression, nausea, constipation, diuresis and euphoria and they are also addictive). In some patients, particularly in the chronically ill, the opioid side effects make it impossible to continuously administer sufficiently high dosages to adequately control pain over the needed period of time. There are also some pain conditions that do not sufficiently respond to opioid pain treatment alone. Therefore, there is a constant need for improved opioid containing analgesic combinations with increased analgesic activity which comprise opioid and non-opioid analgesically active agents and which offer the possibility of reducing the opioid dose needed for efficient pain relief and thereby also reducing the opioid side effects that might result from the otherwise required higher dosages.

Recently, Hartmann (U.S. Pat. No. 6,150,524) and Nagase (U.S. Pat. No. 6,177,438) have discovered morphine derivatives through modifying the structure of morphine so as to reduce the adverse effects associated with the use of morphine. The results based upon animal studies, however, are still insufficient to support pharmaceutical use in humans with acceptable safety and efficacy.

On the other hand, sodium channel blocking compounds that bind to the SS1 or SS2 subunit of a sodium channel, particularly tetrodotoxin and saxitoxin, are found to possess a potent analgesic property (U.S. patent application Ser. No. 09/695,053). Tetrodotoxin is effective on all severe chronic pains. Tetrodotoxin is capable of providing analgesia in a mammal experiencing acute or chronic pain.

In one embodiment, tetrodotoxin (TTX) was found to be about 3,000 times more analgesically potent than morphine. Moreover, TTX does not produce addiction. Furthermore, trials in humans indicate that TTX also provides a duration of action much longer than morphine. TTX provides significant analgesia for pain from chemical stimulation. However, a larger dose appears to be necessary for suppressing pain induced by heat. In studies of use of TTX to treat addiction, experiments suggest a steep dose-toxicity curve for TTX. Therefore, there is a need to improve safety by reducing the TTX dose needed for efficient pain relief.

Fairbanks (U.S. Pat. No. 6,204,271) introduced co-administration of an opioid analgesic agent and moxonidine as a non-opioid agent for producing synergistic analgesia in mammals, hoping to provide a reduced propensity for causing undesirable side effects. Moxonidine is known to be an imidazoline/$\alpha_2$-adrenergic ($I_1/\alpha_2$-AR) receptor agonist and is clinically used in antihypertensive medications. Monoxidine is reported to have analgesic activity, but is not comparable to TTX, which is potent and provides long duration of relief in cancer patients. TTX is also non-addictive as shown through studies in a variety of animals.

SUMMARY OF THE INVENTION

The present invention is related to producing analgesia in mammals, in particular in humans, by co-administering synergistically effective amounts of (1) a sodium channel blocking compound that specifically binds to the SS1 or SS2 subunit of a sodium channel, such as tetrodotoxin or saxitoxin or analogs thereof; and (2) an opioid analgesic agent. The present invention further pertains to analgesic pharmaceutical compositions comprising synergistically effective amounts of a sodium channel-blocking compound that specifically binds to the SS1 or SS2 subunit of a sodium channel and an opioid analgesic agent.

An object of this invention is to provide a potent analgesic composition containing a long-acting analgesic sodium channel-blocking compound that binds to the SS1 or SS2 subunit of a sodium channel, and an opioid analgesic agent, with a reduced propensity for causing undesirable adverse effects.

It is also an object of the invention to provide a non-addictive sodium channel blocker with analgesic activity showing synergy with the analgesic activity of the opioid, and to provide analgesic compositions comprising an opioid analgesic agent, such as morphine and its derivatives, and such a synergistically effective non-addictive sodium channel blocker which allows reducing the amount of the opioid necessary to achieve effective pain treatment.

It is further an object of the invention to present a method for producing analgesia induced by opioids or sodium channel blockers that binds to the SS1 or SS2 subunit in larger mammals, particularly in humans, whereby undesirable side effects of acute and chronic administration of strong opioids and said sodium channel blockers are reduced.

BRIEF DESCRIPTION OF THE DRAWINGS

FIG. 1 shows the analgesia effect of co-administered TTX and morphine observed in the formalin-induced inflammatory pain test in rats.

FIG. 2 shows the actual and the theoretical predictive analgesia effect of TTX at 0.19 $\mu$g/kg co-administered with morphine observed in the formalin-induced inflammatory pain test in rats.

FIG. 3 shows the actual and the theoretical predictive analgesia effect of TTX at 0.39 $\mu$g/kg co-administered with morphine observed in the formalin test in rats.

FIG. 4 shows the actual and the theoretical predictive analgesia effect of TTX at 0.39 µg/kg co-administered with morphine observed in the tail-flick test in mice.

FIG. 5 shows the actual and the theoretical predictive analgesia effect of TTX at 0.79 µg/kg co-administered with morphine observed in the tail-flick test in mice.

DETAILED DESCRIPTION OF THE INVENTION

The present invention is related to producing analgesia in mammals, in particular in humans, by co-administering synergistically effective amounts of (1) a sodium channel blocking compound that specifically binds to the SS1 or SS2 subunit of a sodium channel; and (2) an opioid analgesic agent. In such a combination, the opioid agent or a pharmaceutically acceptable derivative or salt thereof, can be administered in a low-analgesic dose, or even in a per se sub-analgesic dose. The composition may contain both, a sodium channel blocking compound that specifically binds to the SS1 or SS2 subunit of a sodium channel and the opioid agent, together in one dosage form or each in a separate dosage form.

Tetrodotoxin and saxitoxin are known to be sodium channel-blocking compounds that specifically bind to the SS1 or SS2 subunit of a sodium channel.

Tetrodotoxin and its pharmacologically acceptable salts are species of octahydro-12-(hydroxymethyl)-2-imino-5,9:7,10a-dimethano-10aH-[1,3]dioxocino[6,5-d]-pyrimidine-4,7,10,11,12-pentol derivatives that may be used in accordance with the invention. The chemical name of tetrodotoxin and other related data are shown below:

Chemical name: octahydro-12-(hydroxymethyl)-2-imino-5,9:7,10a-dimethano-10aH-[1,3]dioxocino[6,5-d]pyrimidine-4,7,10,11,12-pentol Molecular formula: $C_{11}H_{17}N_3O_8$ Molecular weight: 319.27.

Structure:

TTX compounds can be manufactured in a known manner essentially in accordance with the processes described in U.S. patent applications Ser. Nos. 09/695,711, 09/818,775, and 09/818,863 or in a manner similar to these processes.

Saxitoxin (STX) and its pharmacologically acceptable salts are species of 2,6-diamino-4-((aminocarbonyl)oxy)methyl-3a,4,8,9-tetrahydro-1H,10H-pyrrolo(1,2-c)purine-10,10-diol(3aS-(3a-a-a-4-a,10aR*)) derivatives which may be used in accordance with the invention.

The chemical name of saxitoxin and other related data are shown below:

Chemical name: 2,6-diamino-4-((aminocarbonyl)oxy)methyl-3a,4,8,9-tetrahydro-1H,10H-pyrrolo(1,2-c)purine-10,10-diol(3aS-(3a-a-a-4-a,10aR*))

Molecular formula: $C_{10}H_{17}N_7O_4$

Molecular weight: 299.3.

Structure:

One of the findings in this invention is that tetrodotoxin synergizes with the analgesic activity of opioids, in particular opioids such as morphine, when tetrodotoxin and such an opioid analgesic are co-administered for the treatment of pain. This co-administration results in a greater-than-additive effect.

According to U.S. patent application Ser. No. 09/695,053, TTX and STX possess similar modes of action and toxicity. Therefore, the inventors suggest that STX is also synergistic with the analgesic activity of opioids at similar dosage ranges.

Opioid or opiate is a general term for natural or synthetic substances that bind to specific receptors ("opioid receptors") in the central nervous system, producing an agonist action. At present two types of opioid receptors, $\mu$- and $\delta$ are known. Also two subtypes of $\mu$ receptors, $\mu 1$ and $\mu 2$ are known. Opioid analgesics are extremely useful in managing severe acute pain, postoperative pain and chronic pain including cancer pain. Typical opioid analgesics are morphine, codeine, methadone and fentanyl. These analgesics can be used in the invention. Opioid agonists with opioid receptor activity, like morphine and compounds structurally related to morphine, or compounds functionally related to morphine such as deltorphin II, or pharmaceutically acceptable derivatives or salts thereof, can be used in the invention. Fentanyl, remifentanil, etc., are further examples of opioid analgesics used in clinical treatment that can be employed. Morphine is most preferably used as the opioid. Suitable pharmaceutically acceptable salts of opioids include hydrochlorides, hydrobromides, hydroiodides, sulphates, bisulphates, phosphates, acetates, nitrates, citrates, tartrates, bitartrates, terephthalates, succinates, malates, maleates, fumarates, pectinates and pamoates. Preferably, the pharmaceutically acceptable salt of morphine is a hydrochloride, a sulphate or a tartrate.

Nociception is a processing reaction by the central nervous system to the transmission of stimulation of nociceptors. Noxious stimuli can cause depolarization in the primary perceptive nerve endings so as to excite the nociceptor receptors. The nociceptors indeed are the nerve endings of neurons that have their cell bodies outside the spinal column in the dorsal root ganglion. The true nociception neurons are the myelinated fibers (Aδ) and unmyelinated fibers (C-fibers). Nociception acts also like an alarm to induce escape or defense reactions against noxious stimuli.

Tetrodotoxin has long been considered interesting for its action of altering the pain caused by nociception. According to Catterall, in animal models of neuropathic pain in rats, tetrodotoxin inhibits the ectopic discharges originating at related dorsal root ganglia (DRG) and dorsal horn (DH) of the spinal cord and hyperexcitability of neurons, and increases the reaction threshold of pain receptors. As Kostyun et al. pointed out that at least two types of voltage-dependent sodium channels exist in the dorsal root ganglion neurons of a mammal, i.e., the TTX-S sodium channel that is sensitive to tetrodotoxin and manifests rapid inward ionic currents, and the TTX-R channel that is resistant to tetrodotoxin and manifests slower inward ionic currents.

Peripheral application of TTX blocked the fast excitatory postsynaptic potentials (EPSP) evoked by electrical stimulation but failed to block the electrically evoked slow EPSPs (Srdija Jeftinija). This finding provides an explanation of the result that TTX produced only 71.7% inhibition even at a dose of 2.5 $\mu$g/kg in the formalin test model in rats.

Morphine as a classic analgesic produces pain inhibition primarily via $\mu$ receptors (Besse, D. et al.). A recent study shows that morphine can block the excitatory amino acid mediated membrane current in ambignal motoneurons of the rat, produce hyperpolarization in the membrane potential, and cause EPSPs to disappear (Zhang, M. et al.).

North concluded that morphine can increase a potassium conductance and produce hyperpolarization by exciting $\mu$ receptors. In addition, the disappearance of EPSPs may result from the inhibition of the entry of calcium and sodium ions. Further study by Hung et al. shows that the inhibition by morphine of sodium channels is not caused by direct stimulation to opioid receptors, but rather is related to delay in the recovery rate of inactivated sodium channels.

Without being bound by any theory of the invention, in view of the blocking action of TTX and morphine on sodium channels, the inventors believe the synergistic analgesic effect of co-administering a trace amount of TTX and a small morphine dose, occurs by tetrodotoxin inhibiting the transmission of noxious stimulation to the spinal column, while morphine produces a central blockade of sodium currents.

The inventors studied the synergistic analgesic action in two animal pain models. According to the invention, by co-administering an opioid with a trace amount of tetrodotoxin, equal pain relieving effects may be achieved with dosages that are substantially reduced as compared to the dosages needed when the opioid is administered alone. In the model of formaldehyde (formalin) induced inflammatory pain in rats, the $ID_{50}$ dose of morphine was reduced 16-fold. Clear synergistic action was observed when TTX at the dose of 0.19 $\mu$g/kg ($\frac{1}{100}LD_{50}$) was given in combination with morphine, respectively at doses of 0.08, 0.15, 0.20, 0.60, 1.25, 2.5 mg/kg, as shown in FIG. 2. TTX at the dose of 0.39 $\mu$g/kg co-administered with morphine at 0.15 mg/kg also produced a synergistic effect (FIG. 3).

In the other nociceptive pain model, heat-induced tail-flick in mice, the $ED_{50}$ of morphine was reduced 2 to 5 fold, and the duration of action was prolonged significantly.

Therefore, the combination of tetrodotoxin and morphine will either produce positive synergistic analgesic action, or at least produce equal analgesic effect at lower dose levels for both, establishing the feasibility of the present invention.

Tetrodotoxin produces pharmacological effects on the cardiovascular system, analgesia and local anesthesia. In particular, it provides significant alleviation of various dull pains and stinging pains without causing addiction. Based upon the findings of the present invention, the safety and efficacy of TTX can be improved by lowering the dose necessary for treating pain through synergistic action. Opioid analgesic agents, such as morphine, are of limited use because they readily induce tolerance, dependence and addiction. By co-administration of small morphine doses and trace amounts of TTX, this invention provides a novel solution that markedly improves anesthesia effect and substantially reduces undesirable adverse effects. In terms of weight, the proportions of sodium channel blocker and opiate for co-administration will be preferably from 1:100 to 1:30,000, more preferably from 1:200 to 1:5,000, still more preferably from 1:500 to 1:2000.

As compounds, preferred combinations of the sodium channel blocker and opiate are TTX or STX combined with morphine or codeine or fentanyl.

EXAMPLES

The following examples illustrate the methods and compositions of the invention, but are in no way intended to limit the invention.

Example 1

Formalin Induced Inflammatory Pain Test in Rats

In this example, the synergistic analgesia effect produced by co-administering tetrodotoxin and morphine was observed in a formalin test in rats.

1. Materials and Methods 1.1 Animal

Wistar male rats having a body weight between 180–300 grams, first class, QA No. 013056, supplied by the Experimental Animal Center of Medical Branch, Beijing University.

1.2 Test Article and Reagents

Tetrodotoxin powder, purity 95%, Nanning Maple Leaf Pharmaceutical Co., LTD., batch no. 0324C. Before use, the powder was dissolved into an acetic acid solution at the required concentrations and stored at 4° C. in a refrigerator.

Morphine hydrochloride powder, batch no. 960802, Qinghai Pharmaceutical Plant.

Formaldehyde (formalin), batch no. 9401002, Beijing No. 3 Chemical Plant. Prepared to the required concentrations before use.

1.3 Method

The method described by Vogel et al. was followed. Having a body weight between 180–220 grams, 228 male Wistar rats were randomly divided into 24 groups. They were not given food, only water ad-libitum during the 12 hours prior to dosing. The rats were dosed intramuscularly with a normal saline solution (control), morphine hydrochloride (0.08–10.00 mg/kg) or TTX at 0.39 $\mu$g/kg or 0.19$\mu$g/kg; or by co-administering intramuscularly TTX at 0.39$\mu$g/kg+morphine (0.08–2.50 mg/kg), or TTX at 0.19 $\mu$g/kg+morphine (0.08–5.0 mg) on either side of a rat. The injection volume was 0.1 mL/100 gram body weight. At 40 minutes after dosing, each rat was given subcutaneously 0.06 mL of 2.5% formalin in the plantar surface of the right paw. Then the animal was put into a 12 cm×12 cm×12 cm polymethyl methacrylate box to observe. Its reactions to pain were monitored in the following 5 minutes. The analgesia effect would be manifested if the animal put all its paws on the floor and indicated no preference to the treated paw. Parameter signs included twitching, lifting, licking or gnawing the treated hind paw. The painful response scores were calculated as per the following formula: licking/gnawing time (sec)×3+twitching occurrences×⅔+lifting time (sec).

The pain response scores of the TTX groups were compared with those of the control groups, and the following formula was used to calculate the inhibition rate of TTX on pain responses:

Inhibition rate (%)=(the average of the pain response scores of the control group−that of the TTX group)/the average of the pain response scores of the control group×100%

The medium inhibition dose, $ID_{50}$, was calculated by the Logit method.

1.4 Results

During preliminary tests, no significant differences were observed among the results of normal saline, buffer solution and normal saline plus buffer solution. Therefore, only normal saline was used as a control in the formal tests. Neither administering on both sides of an animal nor variance in injection volumes were taken into consideration for co-administering groups.

As shown in Table 1 and FIG. 1, the half inhibition dose ($ID_{50}$) of morphine in the model of formalin-induced pain in rats was 2.30 mg/kg body weight. A trace amount of TTX, 0.19 μg/kg or 1/100 of $LD_{50}$, produced an inhibition rate of 11.6% when used alone, but effected significant analgesia when co-administered with a small dose of morphine, e.g., increasing the inhibition rate to 63.7% in combination with 0.30 mg/kg of morphine. Morphine used alone at 0.30 mg/kg only produced 10.2% inhibition. Combination of TTX at 0.19 μg/kg with morphine at 2.50 mg/kg increased the inhibition rate to 86.7% from 34.9% where the latter was used alone. TTX at a dose of 0.39 μg/kg (1/50 of $LD_{50}$) produced an inhibition rate of 32.9% when used alone and 66.2% in combination of 0.15 mg/kg of morphine, whereas the latter only produced an inhibition rate of 7.2% when used alone. Analgesia effect increased with the morphine doses in other groups but not significantly.

Example 2

Heat Induced Tail Flick Latency Test in Mice

In this example, the synergistic analgesia effect produced by co-administering tetrodotoxin and morphine was observed through heat-induced tail-flick test in mice.

1. Materials and Methods 1.1 Animal

Kunming mice having a body weight between 12–22 grams, first class, QA No. 013056, supplied by the Experimental Animal Center of Medical Branch, Beijing University.

1.2 Test Article and Reagents

Tetrodotoxin powder, purity 95%, Nanning Maple Leaf Pharmaceutical Co., LTD., batch no. 0324C. Before use, the powder was dissolved into an acetic acid solution to the required concentrations and stored at 4° C. in a refrigerator.

Morphine hydrochloride powder, batch no. 960802, Qinghai Pharmaceutical Plant.

Formaldehyde, batch no. 9401002, Beijing No. 3 Chemical Plant. Prepared to the required concentrations before use.

1.3 Method

The method of heat stimulation-induced tail-flick in mice was used to assess the analgesia effect of co-administering TTX and morphine. A one fold increase in pain threshold/latency was adopted as the criterion for determining the doses of morphine, either used alone or in combination with TTX at 0.79 μg/kg (1/25 $LD_{50}$) and 0.39 μg/kg (1/50 $LD_{50}$), and $ED_{50}$ was calculated by the probit method. For co-administeration, TTX and morphine were given intramuscularly on either side of an animal.

Dosage Determination

Where morphine was given alone, the upper and lower limits of dosage and a progression ratio were determined through preliminary tests so as to calculate the doses for four animal groups. Likewise, the morphine doses were determined for co-administeration with TTX at doses of 0.79 μg/kg (1/25 $LD_{50}$) and 0.39 μg/kg (1/50 $LD_{50}$), respectively.

Animal Grouping 320 screened mice, half male and half female, were randomly divided into 16 groups. They were not given food, only water 12 hours prior to dosing. Rats were dosed with a saline solution as a control, morphine hydrochloride (0.01–1.80 mg/kg), TTX X2 at 0.79 μg/kg (1/25 $LD_{50}$) and 0.39 μg/kg (1/50 $LD_{50}$), and 12 co-administering groups of TTX at 0.79 μg/kg in combination of morphine (0.004–0.33 mg/kg) and TTX at 0.39 μg/kg in combination with morphine (0.01–1.50 mg/kg), respectively.

The heat tail flick analgesia meter includes a heat source consisting of a 12 V, 50 watt, 8.75 mm projector lamp. The light beam from the heat source was focused and directed to a point on the tail of a mouse being tested, having a distance of 1–2 mm plus 1/3 of the tail length to the tail end.

The test drugs were given intramuscularly. TTX, morphine or a mixture of the two was injected into the gluteal muscle on either side of the animal in a volume of 0.1 mL/10 g body weight. The tail-flick latencies, which were assessed in response to a noxious heat stimulus, i.e., the response time from applying radiant heat on the dorsal surface of the tail to the occurrence of tail flick, were measured and recorded at 15, 30, 45, 60, 90, 120, 150, 180 min. after dosing. For each measurement, three readings were made consecutively one minute apart, and their average was recorded as the latency. The testing on one animal would be terminated when tail-flick was not observed within 20 seconds, and the latency would be recorded as 20 seconds. The pain inhibition rate was calculated according to the following formula for the purpose of assessing the analgesia potency:

Inhibition rate (%)=[(observed latency−latency of control)/light-deactivation time]×100

1.4 Statistics

The results were processed with SPSS, a statistical software provided by SPSS, Inc. of Chicago, Ill., USA. Half effective dose ($ED_{50}$) and half inhibition dose ($ID_{50}$) were calculated with the probit method. The synergistic action of TTX and morphine was evaluated by an isobologram.

2. Results

As shown in Tables 2 and 3, $ED_{50}$ for morphine used alone was 0.41 mg/kg at 45 min after dosing, providing the criterion of one fold increase in latency for the heat-induced tail flick test in mice. Co-administered with TTX at a dose of 1/25 $LD_{50}$ (0.79 μg/kg), the $ED_{50}$ of morphine decreased to 0.07 mg/kg. When co-administered with TTX at a dose of 1/50 $LD_{50}$ (0.39 μg/kg), the $ED_{50}$ of morphine decreased to 0.21 mg/kg.

Providing the basic latency as a criterion, $ID_{50}$ for morphine used alone was 0.33 mg/kg at 45 min after dosing. Co-administered with TTX at small doses of 0.79 μg/kg and 0.39 μg/kg, the $ID_{50}$ of morphine decreased respectively to 0.08 mg/kg and 0.15 mg/kg, or only ¼ and ½ of the $ID_{50}$ for morphine used alone.

For practical use of the synergistic interaction between an opioid analgesic agent and a compound that binds to the SS1 or SS2 subunit of a sodium channel, it is helpful to characterize the toxicity resulting from co-administration thereof, and subsequently to elicit the optimal analgesic proportions in the combination or composition thereof. Therefore, test protocols are designed for this purpose as shown in Example 3–6.

Example 3

Toxicity of TTX and Morphine Co-Administered by Intramuscular Injection in Rats

This test is intended to measure the toxicity interaction of TTX and morphine through determining and comparing the half death doses ($LD_{50}$) of morphine, and co-administered TTX and morphine. The LD50 of TTX is known from U.S. patent application Ser. No. 09/695,053. The method will follow the test for determining acute toxicity. Toxicity of the combination of TTX and morphine will be examined in two proportions to obtain the $LD_{50}$ values, respectively.

Wistar rats, having a body weight between 200–220 grams each, will be randomly divided into 12~15 groups of 10, half male and half female; and each test drug or combination will use 4~5 groups of animals. They will be allowed no food, only water ad-libitum during the 12 hours before dosing. For determining $LD_{50}$ of TTX or morphine individually, each animal will receive one administration of the test drug. For co-administration of TTX and morphine, each animal will be given TTX and morphine on either side (in separate dosage forms) or one administration of TTX and morphine in a singular dosage form. After dosing, the animals will be monitored with respect to toxic reactions and death for seven consecutive days. Autopsy will be conducted on any dead animals immediately, with general examination for toxic reactions in major organs.

Consequently, the $LD_{50}$ values will be determined by the Bliss method. If the $LD_{50}$ increases significantly by comparison with the theoretical additive, the toxicity of co-administeration is lower than that of TTX or morphine individually used, indicating improved safety in light of the synergistic analgesic action between TTX and morphine. Even if the $LD_{50}$ remains unchanged, the combined use of TTX and morphine can still be desirable.

Example 4

Isobolographic Profile for the Interaction between TTX and Morphine by the Pain Model of Formalin-Induced Inflammation in Rats The isobologram is a commonly used technique to establish superadditive, subadditive, or merely additive effects resulting from the administration of two compounds. The design of this test follows Tallarida's method, which was also adopted in U.S. Pat. No. 5,468,744. As mentioned above, the purpose is to elicit the optimal analgesic proportions in the combination or composition of TTX and morphine, in light of the findings of toxicity interactions in Example 3. The pain model of formalin test in rats will be used to assess the analgesic effects of the test drug or combinations, particularly, to determine the half inhibition doses ($ID_{50}$). For determining $ID_{50}$ of TTX or morphine individually, each animal will receive one administration of the test drug. For co-administration of TTX and morphine, each animal will be given TTX and morphine on either side (in separate dosage forms) or one administration of TTX and morphine in a single dosage form. The proportions of TTX and morphine in terms of weight for co-administration will be between 1:200 to 1:5,000. The number of particular proportions/animal groups will be determined based upon these proportion ranges so that sound and sufficient data can be made available for one person in the art with ordinary skills to draw and interpret isobolograms thereupon.

Example 5

Toxicity of Saxitoxin (STX) and Morphine Co-Administered by Intramuscular Injection in Rats As in Example 3, this test is intended to conclude the toxicity interaction of STX and morphine through determining and comparing the half death doses ($LD_{50}$) of STX, morphine, and co-administered STX and morphine. Toxicity of the combination of STX and morphine will be examined in two proportions to obtain the LD50 values, respectively.

Wistar rats, half male and half female, having a body weight between 200–220 grams each, will be randomly divided into 16~20 groups of 10, and each test drug or combination will use 4~5 groups of animals. The test method and procedure will follow Example 3, as will the analysis of the toxicity interaction between STX and morphine and the feasibility of their combination use.

Example 6

Isobologram Profile for the Interaction between STX and Morphine by the Pain Model of Formalin-Induced Inflammation in Mice The method will follow Example 4, replacing TTX with STX. In terms of weight, the proportions of STX and morphine for co-administration will be preferably between 1:200 to 1:5,000.

References

Various articles of the scientific and patent literature are cited herein. Each such article is hereby incorporated in its entirety and for all purposes by such citation.

1. Hartmann, et al., Morphine derivatives with analgesic activity, U.S. Pat. No. 6,150,524, 2000.
2. Nagase, et al., Morphine derivatives and pharmaceutical use thereof, U.S. Pat. No. 6,177,438, 2001.
3. Dong, Q. B. et al., A Method of Analgesia, U.S. patent application Ser. No. 09/695,053, 2000.
4. Adams, et al. Synergistic local anesthetic compositions, U.S. Pat. No. 4,022,899, 1977.
5. Catterall W A. Cellular and molecular biology of voltage gated sodium channels. Physiol Rev. 1992;72;s15–s18.
6. Kostyun, P. G., Veselovsky, N. S and Tsyndrenko, A. Y., Ionic currents in the somatic membrane of rat dorsal root ganglion neurons. I. Sodium current, Neuroscience, 6(1981) 2423–2430.
7. Srdija Jeftinija, The role of tetrodotoxin-resistant Sodium channels of small primary afferent fibers. Brain Research 639 (1994) 125–134.
8. U.S. patent application Ser. No. 09/695,053, 2000.
9. Besse, D., Lombard, M-C. And Besson, J-M (1991) Autoradiographic distribution of mu, delta and kappa opioid binging sites in the superficial dorsal horn, over the rostrocaudal axis of the rat spinal cord. Brain Res., 548:287–291.
10. Zhang M, Nie L, Liu L, Wang Y T, Neuman R S, Bieger D. Morphine blocked the exitatory amino acid mediated membrane current in ambignal motoneurons of the rat. Acta Physiologica Sinica, 1995,47(3),253–258.
11. North, R. A. and Williams, J. T. (1985). On the potassium conductance increased by opiates in rat brains coeruleus neurones. J. Physiol., 364,265–280.
12. C.-F. Hung, C.-H. Tsai and M-J. Su, Opioid receptor independent effects of morphine on membrane currents in single cardiac myocytes, British Journal of Anesthesia 1998;81:925–931.
13. H. Gerhard Vogel, Wolfgang H. Vogel, Guide to pharmacological tests-new drug discovery and pharmacological evaluation, translated by Guanhua Du et al., Sciences Publishing of China, 2001, 499–500.
14. Duanzheng Xu, Application of bio-statistics in pharmacology, Sciences Publishing of China, 1986, 357–366.
15. Tallarida, R. J. et al., Statistical analysis of drug-drug and site-site interactions with isobolograms, Life Sci. 1989; 45: 947–961.
16. Zhang, W. et al., Statistics and Programs of Pharmacology, Beijing People's Health Publishing Service. 1988; 108–116.

TABLE 1

Analgesia effect of co-administered TTX and morphine:
formalin test in rats

| Test drug | Dose (mg/kg) | Animal number | Pain reaction score | Inhibition rate (%) | $ID_{50}$ of morphine (mg/kg) |
|---|---|---|---|---|---|
| Normal saline | | 8 | 252.3 ± 105.4 | | |
| TTX | $0.19 \times 10^{-3}$ | 10 | 223.0 ± 58.3 | 11.6 | |
| | $0.39 \times 10^{-3}$ | 10 | 169.1 ± 47.2 | 32.9 | |
| Morphine | 0.08 | 8 | 243.8 ± 36.4 | 3.4 | |
| | 0.15 | 8 | 234.0 ± 26.9 | 7.2 | |
| | 0.30 | 8 | 226.5 ± 73.5 | 10.2 | |
| | 0.60 | 8 | 274.3 ± 119.5 | 11.0 | 2.30 |
| | 1.25 | 8 | 190.3 ± 129.9 | 24.6 | (1.38 ~ 4.26) |
| | 2.50 | 8 | 164.3 ± 82.0 | 34.9 | |
| | 5.00 | 8 | 49.8 ± 34.1 | 80.2 | |
| | 10.00 | 8 | 5.6 ± 6.5 | 97.7 | |
| TTX ($0.39 \times 10^{-3}$ mg/kg) + morphine | 0.08 | 8 | 162.9 ± 55.4 | 35.4 | |
| | 0.15 | 20 | 85.3 ± 54.2 | 66.2 | |
| | 0.30 | 14 | 138.0 ± 50.7 | 45.3 | |
| | 0.60 | 14 | 119.5 ± 38.3 | 52.6 | |
| | 1.25 | 14 | 109.3 ± 64.4 | 56.7 | |
| | 2.50 | 8 | 71.6 ± 44.2 | 71.6 | |
| TTX ($0.19 \times 10^{-3}$ mg/kg) + morphine | 0.08 | 8 | 132.0 ± 39.3 | 47.7 | |
| | 0.15 | 10 | 94.1 ± 43.9 | 62.7 | |
| | 0.30 | 8 | 91.6 ± 51.3 | 63.7 | |
| | 0.60 | 8 | 146.8 ± 66.6 | 41.8 | |
| | 1.25 | 8 | 139.4 ± 68.9 | 44.7 | |
| | 2.50 | 8 | 36.6 ± 16.3 | 86.7 | |
| | 5.00 | 8 | 24.4 ± 12.1 | 90.3 | |

TABLE 2

Analgesia effect of co-administered TTX and morphine - $ID_{50}$ (heat induced tail flick test in mice, latency Mean ± SD, n = 20), compared with the $ID_{50}$ for morphine used alone.

| Group | Dose (mg/kg) | Latency before dosing | Latency after dosing | Inhibition rate (%) | $ID_{50}$ & 95% Confidence Limits |
|---|---|---|---|---|---|
| Control (normal saline) | | 5.36 ± 0.96 | 5.43 ± 0.89 | 1.29 | |
| TTX | $0.79 \times 10^{-3}$ | 5.25 ± 0.59 | 6.04 ± 0.76 | 12.06 | |
| | $0.39 \times 10^{-3}$ | 5.56 ± 0.81 | 5.88 ± 1.00 | 5.44 | |
| Morphine hydrochloride | 0.01 | 5.48 ± 1.44 | 6.35 ± 1.87 | 13.70 | |
| | 0.06 | 5.83 ± 1.49 | 8.67 ± 2.54 | 32.76 | 0.33 |
| | 0.33 | 5.21 ± 1.39 | 10.04 ± 2.49 | 48.11 | (0.21 ~ 0.55) |
| | 1.80 | 5.63 ± 1.31 | 18.94 ± 1.02 | 70.27 | |
| TTX (0.79 ug/kg) + morphine hydrochloride | 0.004 | 5.83 ± 1.26 | 7.22 ± 1.14 | 19.25 | |
| | 0.016 | 6.37 ± 1.08 | 9.96 ± 2.40 | 36.04 | 0.08 |
| | 0.073 | 5.78 ± 1.29 | 11.82 ± 2.65 | 51.09 | (0.05 ~ 0.14) |
| | 0.330 | 6.31 ± 1.10 | 17.21 ± 2.23 | 63.33 | |
| TTX (0.39 ug/kg) + morphine hydrochloride | 0.01 | 5.76 ± 0.89 | 8.17 ± 1.94 | 29.50 | |
| | 0.05 | 5.84 ± 0.73 | 10.16 ± 1.85 | 42.52 | 0.15 |
| | 0.28 | 5.55 ± 0.88 | 12.50 ± 3.46 | 55.60 | (0.08 ~ 0.33) |
| | 1.50 | 5.61 ± 0.86 | 16.28 ± 2.53 | 65.54 | |

TABLE 3

Analgesia effect of co-administered TTX and morphine - $ED_{50}$ (heat induced tail flick test in mice, n = 20); $ED_{50}$ of morphine by comparison with the latencies at 45 min after dosing.

| Group | Dose (mg/kg) | Positive occurrences | Percentage of positive occurrences (%) | $ED_{50}$ & 95% Confidence Limits | $ED_{95}$ & 95% Confidence Limits |
|---|---|---|---|---|---|
| Control (N.S) | | | | | |
| TTX | $0.79 \times 10^{-3}$ | | | | |
| | $0.39 \times 10^{-3}$ | | | | |
| Morphine Hydrochloride | 0.01 | 0 | 0 | | |
| | 0.06 | 2 | 10 | 0.41 | 0.77 |
| | 0.33 | 7 | 35 | (0.30 ~ 0.84) | (0.54 ~ 1.91) |
| | 1.80 | 20 | 100 | | |

TABLE 3-continued

Analgesia effect of co-administered TTX and morphine - $ED_{50}$ (heat induced tail flick test in mice, n = 20); $ED_{50}$ of morphine by comparison with the latencies at 45 min after dosing.

| Group | Dose (mg/kg) | Positive occurrences | Percentage of positive occurrences (%) | $ED_{50}$ &95% Confidence Limits | $ED_{95}$ &95% Confidence Limits |
|---|---|---|---|---|---|
| TTX (0.79 ug/kg) + Morphine Hydrochloride | 0.004 | 0 | 0 | | |
| | 0.016 | 2 | 10 | 0.07 | 0.13 |
| | 0.073 | 10 | 50 | (0.06 ~ 0.10) | (0.10 ~ 0.22) |
| | 0.330 | 20 | 100 | | |
| TTX (0.39 ug/kg) + Morphine Hydrochloride | 0.01 | 1 | 5 | | |
| | 0.05 | 2 | 10 | 0.21 | 0.42 |
| | 0.28 | 14 | 70 | (0.16 ~ 0.29) | (0.33 ~ 0.62) |
| | 1.50 | 20 | 100 | | |

We claim:

1. A method of producing analgesia in a mammal experiencing pain, comprising administering to the mammal a synergistically analgesic effective combination of an opioid analgesic agent and a compound that binds to the SS1 or SS2 subunit of a sodium channel in a pharmaceutically suitable vehicle.

2. The method of claim 1, wherein the opioid is selected from the group consisting of morphine, codeine, methadone and fentanyl.

3. The method of claim 1, wherein the opioid and the compound that binds to the SS1 or SS2 subunit of a sodium channel are administered together in one single dosage form at synergistically analgesic effective doses.

4. The method of claim 1, wherein the opioid and the compound that binds to the SS1 or SS2 subunit of a sodium channel are administered in separate dosage forms at synergistically analgesic effective doses.

5. The method of claim 1, wherein the administering is intrathecally or intramuscularly.

6. The method of claim 1, wherein the compound that binds to the SS1 or SS2 subunit of a sodium channel is tetrodotoxin or a derivative thereof.

7. The method of claim 1, wherein the opioid is morphine.

8. The method of claim 7, wherein the opioid is morphine.

9. The method of claim 6, wherein the effective dose of tetrodotoxin is from 0.01 μg per kilogram body weight to 20 μg per kilogram body weight.

10. The method of claim 8, wherein the effective dose of morphine is from 0.002 mg per kilogram body weight to 20 mg per kilogram body weight.

11. The method of claim 6, wherein the sodium channel blocking compounds is a composition comprising at least one of tetrodotoxin, anhydrotetrodotoxin, tetrodaminotoxin, methoxytetrodotoxin, ethoxytetrodotoxin, deoxytetrodotoxin or tetrodonic acid.

12. The method of claim 1, wherein the compound that binds to the SS1 or SS2 subunit of a sodium channel is saxitoxin or a pharmaceutically acceptable salt thereof.

13. The method of claim 12, wherein the effective dose of saxitoxin is from 0.01 μg per kilogram body weight to 20 μg per kilogram body weight.

14. The method of claim 13, wherein the saxitoxin is a compound comprising a tetrahydropurine moiety composed of two guanidine units fused together in a stable azaketal linkage, having a molecular formula $C_{10}H_{17}N_7O_4$.

* * * * *